(12) United States Patent
Schena (10) Patent No.: US 12,094,602 B1
(45) Date of Patent: Sep. 17, 2024

(54) VERIFYING A PERFORMANCE OF AN ORAL INSERT

(71) Applicant: Fresh Health Inc., Mountain View, CA (US)

(72) Inventor: Bruce Michael Schena, Menlo Park, CA (US)

(73) Assignee: Fresh Health Inc., Mountain View, CA (US)

( * ) Notice: Subject to any disclaimer, the term of this patent is extended or adjusted under 35 U.S.C. 154(b) by 0 days.

(21) Appl. No.: 18/220,466

(22) Filed: Jul. 11, 2023

(51) Int. Cl.
*G16H 40/40* (2018.01)
*A61C 17/02* (2006.01)

(52) U.S. Cl.
CPC ......... *G16H 40/40* (2018.01); *A61C 17/0211* (2013.01)

(58) Field of Classification Search
None
See application file for complete search history.

(56) References Cited

U.S. PATENT DOCUMENTS

| | | | | |
|---|---|---|---|---|
| 4,422,942 | A * | 12/1983 | Allington | G01N 30/32 210/659 |
| 8,424,551 | B2 * | 4/2013 | Seeli | G06F 30/20 165/173 |
| 2003/0056578 | A1 * | 3/2003 | Mitchell | F02C 9/26 73/112.01 |
| 2009/0061373 | A1 * | 3/2009 | Bannos | F23N 5/022 700/282 |
| 2011/0290034 | A1 * | 12/2011 | McDonnell | A61B 90/70 73/756 |
| 2016/0130543 | A1 * | 5/2016 | Daniele | C12M 29/10 264/41 |
| 2018/0127109 | A1 * | 5/2018 | Freeth | B64D 37/16 |
| 2019/0302022 | A1 * | 10/2019 | Sun | G01N 33/54373 |
| 2020/0308942 | A1 * | 10/2020 | Knoeller | E21B 41/00 |
| 2022/0027526 | A1 * | 1/2022 | Ruedisueli | A46B 11/06 |
| 2022/0176400 | A1 * | 6/2022 | Schlenker | B05B 15/50 |

OTHER PUBLICATIONS

Muzemder et al, "Intra-pore tortuosity and diverging-converging pore geometry controls on flow enhancement due to liquid boundary slip" Journal of Hydrology vol. 598, Jul. 2021, 126475 downloaded from https://doi.org/10.1016/j.jhydrol.2021.126475 (Year: 2021).*
Don "What Is the Difference Between Pressure Control Valve and Flow Control Valve" Feb. 20, 2021 at https://cncontrolvalve.com/what-is-the-difference-between-a-pressure-control-valve-and-a-flow-control-valve/#:~:text=Does%20a%20pressure%20regulator%20affect,flow%20rates%20for%20optimal%20performance (Year: 2021).*

* cited by examiner

Primary Examiner — Michael J Dalbo
Assistant Examiner — Denise R Karavias
(74) Attorney, Agent, or Firm — Van Pelt, Yi & James LLP (57) ABSTRACT

Fluid is provided to a manifold selected among a plurality of manifolds associated with an oral insert. Each of the plurality of manifolds is associated with a same expected performance within a threshold tolerance. An actual performance of the manifold is determined based on a pressure and a flow rate associated with providing the fluid to the manifold. A performance of the oral insert is verified based on whether the actual performance of the manifold matches the same expected performance within a threshold tolerance.

21 Claims, 11 Drawing Sheets

VERIFYING A PERFORMANCE OF AN ORAL INSERT

BACKGROUND OF THE INVENTION

An oral insert comprises an arrangement of fluid nozzles positioned within the oral insert based on the oral or dental structures of the user's teeth to provide a customized fluid flow over the user's teeth. The oral insert includes a plurality of manifolds, each manifold including one or more fluid nozzles. A 3D printer may use a resin to manufacture the oral insert. The oral insert manufactured by the 3D printer may have fluid nozzles that have a size on the order of 750 microns. A post-manufacturing cleaning process may be implemented to remove any residual resin from the oral insert. However, some residual resin may remain in a manifold or a fluid nozzle, which may result in a clogged manifold or a clogged fluid nozzle. A clogged manifold or a clogged fluid nozzle reduces the efficacy of the oral insert in cleaning the oral anatomy of a user.

Each fluid nozzle of the oral insert is associated with an expected performance value. Other systems may individually test the actual performance of each fluid nozzle and compare the actual performance value with the expected performance value. For example, the flow rate of fluid exiting a fluid nozzle may be expected to have a particular flow rate within a threshold tolerance. The oral insert may be determined to be defective in the event the actual performance of at least one of the fluid nozzles does not match the expected performance of the fluid nozzle.

Testing the performance of each fluid nozzle of an oral insert may take a long time to perform or difficult to implement because each test is customized to the oral insert of a user since the location of each oral insert nozzle may be different. Furthermore, the fluid nozzles may have different output angles. The process of testing the fluid nozzles may be the same, but positioning and orienting a sensor at a particular offset from each of the fluid nozzles may introduce delays in the testing process because the tester may need to determine where to test each individual fluid nozzle before the test may commence.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

A technique to verify a performance of an oral insert is disclosed. An oral insert may be manufactured and customized to the oral anatomy of a user. The oral insert is comprised of a fluid inlet port, a plurality of manifolds, a plurality of fluid nozzles, a fluid outlet port, and a tray surface. Each of the plurality of manifolds includes one or more fluid nozzles. In one example, the oral insert may include eight manifolds, each manifold having eight fluid nozzles. The location of the plurality of fluid nozzles is customized to the oral anatomy of the user to direct fluid to clean specific regions of the teeth. For example, some fluid nozzles may be located across from the interproximal spaces and/or along the gingival margins. A direction of a fluid nozzle may also be customized to the oral anatomy of the user. For example, a fluid nozzle may be pointing upwards or downwards.

The oral insert is configured to receive pressurized fluid at the fluid inlet port from a fluid reservoir via a pump. The flow rate associated with the fluid exiting a manifold may be adjusted based on an input voltage associated with the pump. The pressurized fluid is provided to the plurality of fluid nozzles via the plurality of manifolds. The pressure associated with the pressurized fluid decreases as the pressurized fluid is provided from the pump to the plurality of fluid nozzles, however, the plurality of manifolds are designed in a manner such that a flow rate, and thus fluid exit velocity, associated with each of the fluid nozzles is the same within a threshold tolerance. A diameter of a manifold may decrease along a length of the manifold from a fluid inlet port to an end portion of the manifold.

A number of fluid nozzles associated with a manifold may be different than a number of fluid nozzles associated with one or more other manifolds. For example, a first manifold may be associated with seven fluid nozzles and a second manifold may be associated with eight fluid nozzles. This may cause unbalanced pressure drops and uneven fluid flow from the fluid nozzles, that is, the pressure associated with the fluid in the first manifold is different than the pressure associated with the fluid in the second manifold. As a result, the flow rate associated with the first manifold is different than the flow rate associated with the second manifold. This may cause discomfort for the user during a cleaning process. This difference in flow rate may also lead to inconsistent cleaning performance.

When at least one manifold includes a number of fluid nozzles that is different than the number of fluid nozzles associated with the other manifolds associated with the oral insert, the manifold(s) having the different number of fluid nozzles may include one or more flow balancing ports to prevent uneven fluid flow from the fluid nozzles. A flow balancing port may be configured to bleed off a specific amount of excess fluid as fluid flows through the manifold, specifically on manifolds with fewer fluid nozzles than other manifolds in the oral insert.

Other systems may test the performance of a manifold, however, the performance of a manifold may vary depending on the number of fluid nozzles associated with the manifold and whether a manifold having a different number of fluid nozzles than other manifold(s) of the oral insert includes one or more flow balancing ports. Without the use of flow balance port(s), a manifold having seven fluid nozzles may be expected to have a performance that is different than a manifold having eight fluid nozzles.

The disclosed technique enables the performance of manifolds associated with an oral insert to be verified, regardless of whether the number of fluid nozzles associated with each of the oral insert's manifolds are the same. The performance of the manifolds is individually and sequentially tested. A manifold is selected and a resulting PQ (pressure-flow) curve associated with the selected manifold is generated. Fluid is provided to the manifold at a plurality of different flow rates. The flow rate within a manifold may be controlled by adjusting an input voltage (or current) associated with a pump that supplies fluid from a fluid reservoir to the oral insert. A PQ curve associated with the selected manifold is generated by imparting a measured flow rate associated with the manifold and measuring the pressure associated with the manifold inlet of the oral insert, either directly or indirectly, at the plurality of different pump input voltages. The PQ curve is compared to an upper limit curve and a lower limit curve. The upper limit curve and the lower limit curve represent the boundaries of an operational oral insert. The selected manifold and its associated fluid nozzles are determined to be functional in the event the PQ curve is bounded within the upper limit curve and the lower limit curve. The selected manifold and its associated fluid nozzles are determined to be defective in the event at least one point of the PQ curve is outside of the upper limit curve and/or the lower limit curve.

The above process may be repeated for each of the remaining manifolds of the oral insert. However, if a manifold is determined to be defective and there are one or more other remaining manifolds to be tested, the oral insert is determined to be defective. The one or more other remaining manifolds do not need to be tested. As a result, the amount of time and resources needed to verify the performance of the oral insert may be reduced. The oral insert is determined to be operational in response to determining that the corresponding PQ curves associated with each of the manifolds are bounded by the upper limit curve and the lower limit curve.

Figure 1A:
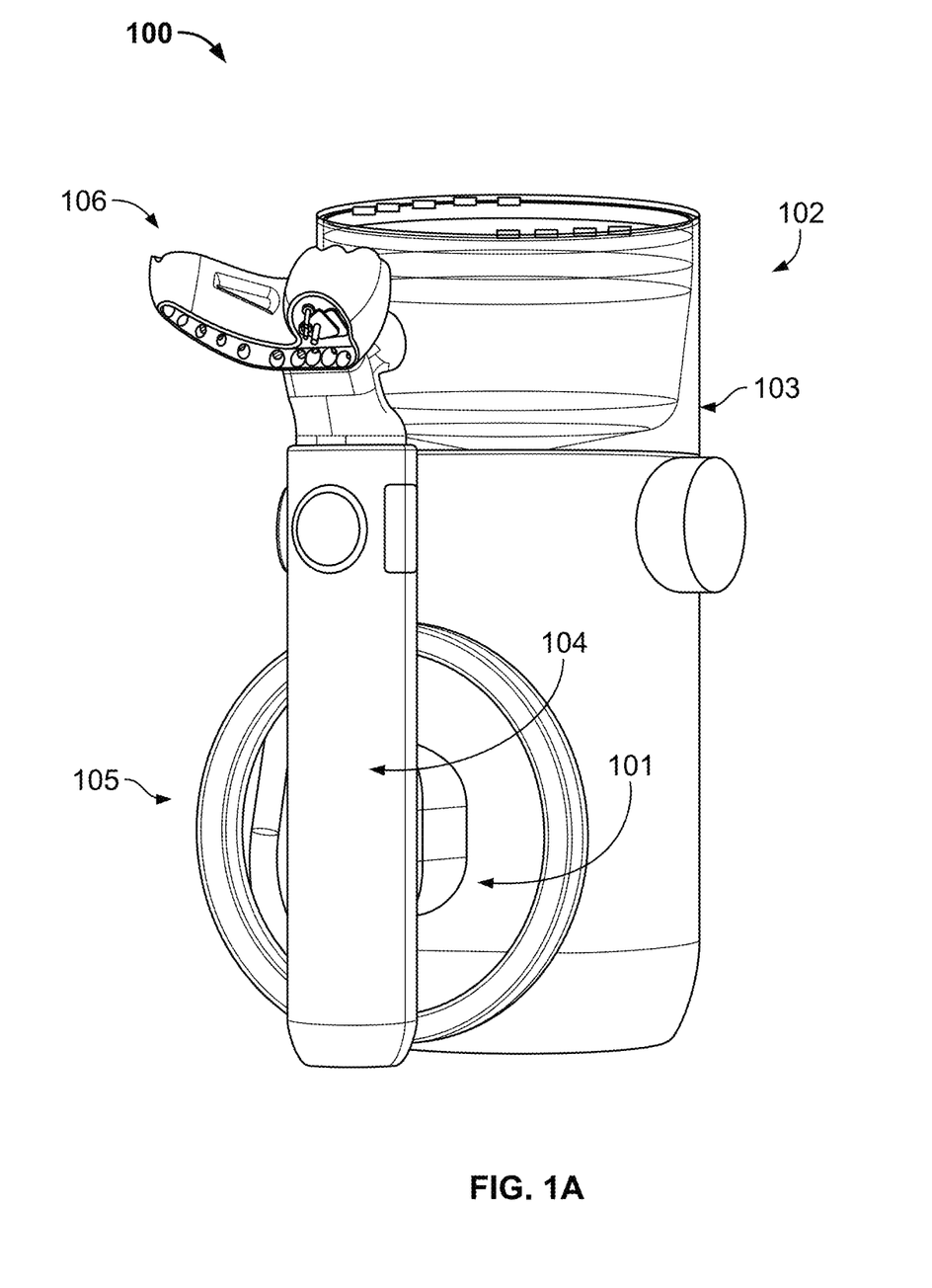
FIG. 1A is a diagram illustrating a system for cleaning the oral anatomy of a user in accordance with some embodiments.

FIG. 1A is a diagram illustrating a system for cleaning the oral anatomy of a user in accordance with some embodiments. In the example shown, system 100 includes a base station 102 having a fluid reservoir 103, a handle 104, and a customized oral insert or mouthpiece 106 coupled to the handle 104. One or more fluid conduits or tubes 105 may connect the fluid reservoir 103 to the handle 104 and to the mouthpiece 106. The handle 104 may comprise one or more control buttons (e.g., a start/stop button, a fluid flow adjustment dial), as may be desirable, which may be positioned variously on the handle for ergonomic or efficient use. In alternative embodiments, system 100 may not have a handle at all, and may alternatively comprise one or more fluid conduits or tubes that directly connect the fluid from the base station reservoir to the mouthpiece. The fluid retained in the fluid reservoir of system 100 may be water, saline, a mouth wash or rinse, (e.g., containing fluoride and/or germicidal or other cleaning and/or teeth protective fluids), and/or any other desirable additive.

The oral insert 106 is comprised of a plurality of fluid nozzles that are arranged in accordance with the unique geometry of the user's oral cavity, gingival geometry, and dental structures (and any oral and/or dental devices or implants). Examples of oral and/or dental devices or implants may include, but are not limited to, permanent and removable dental restorations/prosthetics, orthodontic appliances, and etc. (e.g., crowns, bridges, implants, braces, retainers, dentures, and the like). Each of the fluid nozzles may be positioned to target a specific dental feature. Inside oral insert 106, the fluid nozzles may be connected to one or more internal manifolds. The inlets of these manifolds may extend from the back of the mouthpiece (or where desirable for ergonomic and/or efficient use) in the form of a standardized connector, to which a handle and/or one or more tubes may be connected.

Figure 1B:
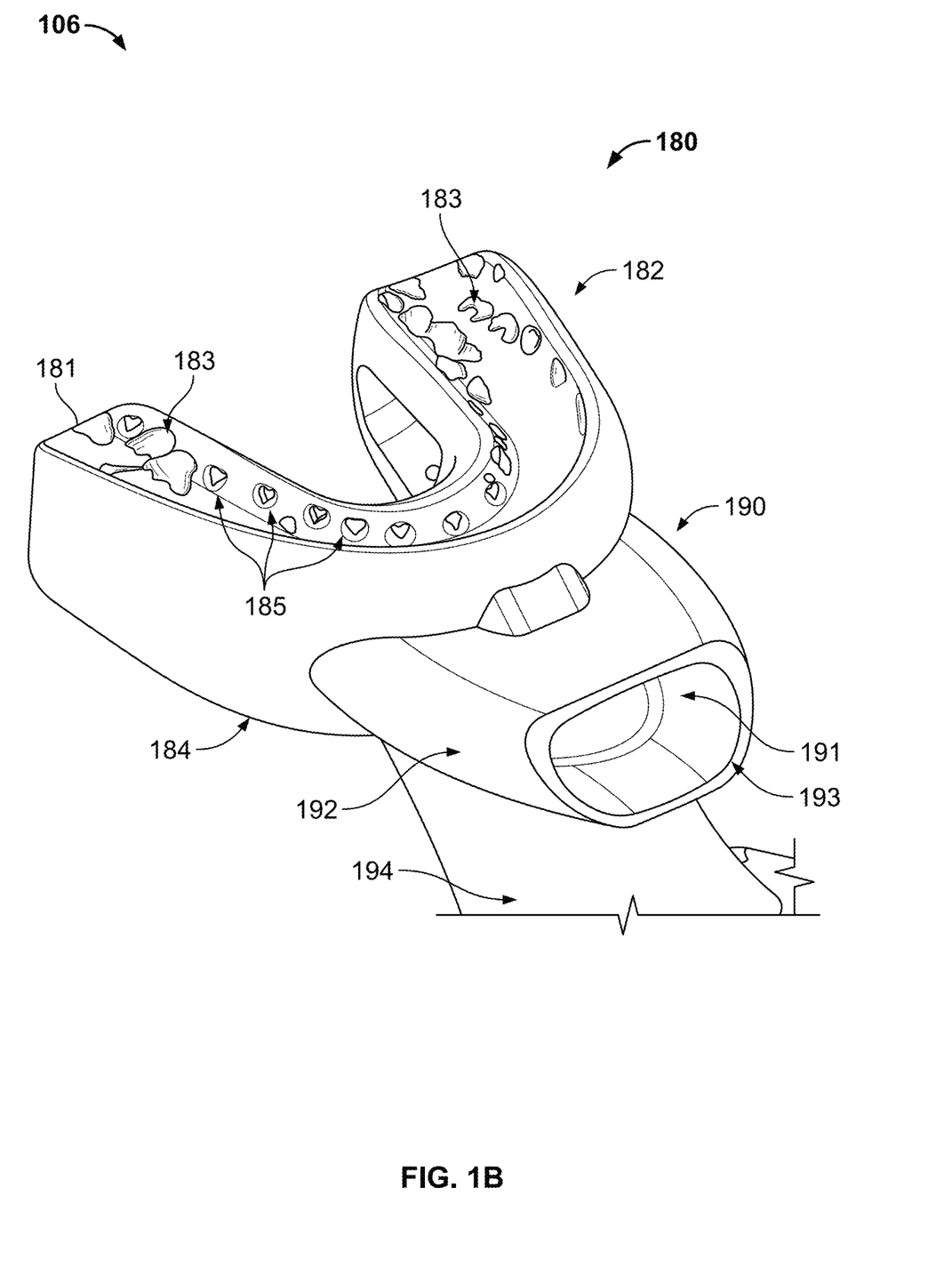
FIG. 1B illustrates a perspective view of an oral insert in accordance with some embodiments.

FIG. 1B illustrates a perspective view of an oral insert in accordance with some embodiments. The oral insert 106 may be made of a rigid material, and may comprise an upper portion 182 having a tray configured to receive a user's upper teeth, a lower portion 184 having a tray configured to receive a user's lower teeth, a plurality of fluid nozzles 186 located in the upper portion and the lower portion, and an effluence conduit 190 located between the upper portion and the lower portion. The trays of the upper and lower portions may comprise one or more alignment features 183, which may comprise protrusions, slots, or recesses that receive and/or articulate with the user's teeth, gums, hard palate, soft palate, other oral structures, and/or may have contours that correspond to one or more teeth. These alignment features may help to ensure that the oral insert is seated in a desired position in the user's mouth. In some variations, one or more of the fluid nozzles 186 may be located in recesses or indentations 185 along the teeth- and/or gingiva-facing surfaces of the upper and lower trays. The recesses 185 and the fluid nozzles 186 may be located at regions of the upper and lower trays that correspond with the interproximal spaces between the user's teeth, and/or at locations that allow the fluid nozzles to direct fluid jets to the interproximal spaces (e.g., that may not necessarily correspond with the locations of the interproximal spaces). The recesses 185 may have a flared or tapered shape, and/or may have one or more concave contours, where the fluid nozzle opening is located at the narrow portion of the recess. The width of the recess may increase as it extends outward from the fluid nozzle opening. The increased width of a flared recess may allow the fluid jet spray to expand unimpeded. In some variations, the central axis of the flared recess may be aligned with the direction of the fluid jet. The effluence conduit 190 may comprise a central port or channel 191 which may extend between a posterior region and anterior region of the oral insert, and may protrude forward at the anterior region as a beak or an elongated spout 192 that terminates at a fluid egress opening 193. The fluid exiting the central port or channel 191 may be provided to a sink or other collection device (e.g., a collector for microbiomes). The central port or channel 191 is configured to have a minimum cross-section area that causes the fluid outputted from effluence conduit 190 to have a particular pressure. The minimum cross-section area is needed to prevent a high back-pressure that would cause discomfort for the user (e.g., a choking feeling) when using oral insert 180. Alternatively or additionally, an effluence conduit may comprise a first side fluid cavity or channel and a second side fluid cavity or channel. The side fluid cavities may funnel into the central port, or may each have their own elongated spouts with separate fluid egress openings. The shape, sizing, and surface contours of the effluence conduit may be configured according to the user's oral anatomy (e.g., size and size of oral cavity, location of teeth, etc.) and configured to promote fluid dynamic efficiency in draining the fluid from the user's mouth. In some variations, the fluid delivered to the user's mouth may be pressurized and/or delivered at a high fluid rate in order to effectively clean their teeth and/or dislodge particles trapped in the interproximal spaces. Because of the increased rate and/or pressure of fluid flow into the oral cavity (i.e., fluid ingress), the effluence conduit of the oral insert may be sized and shaped to allow for fluid egress at the same or greater rate as fluid ingress. The oral insert 106 may also comprise one or more fluid manifolds, which may be a series of branched and/or networked internal fluid manifolds that distribute the fluid from the handle to the individual fluid nozzles. The fluid manifolds may terminate at a series of manifold openings in a manifold connector port 194 of the oral insert. In some variations, the manifold connector may have one opening per fluid manifold, or may have more than one manifold opening per fluid manifold. When the oral insert is connected to the handle, the fluid regulator components may be configured to fluidically engage with the manifold connector such that the fluid regulator controls the fluid flow into the manifolds. Optionally, the fluid regulator in the handle may further comprise a manifold block having a plurality of fluid channels that are configured to be aligned with the manifold openings in the manifold connector.

Figure 1C:
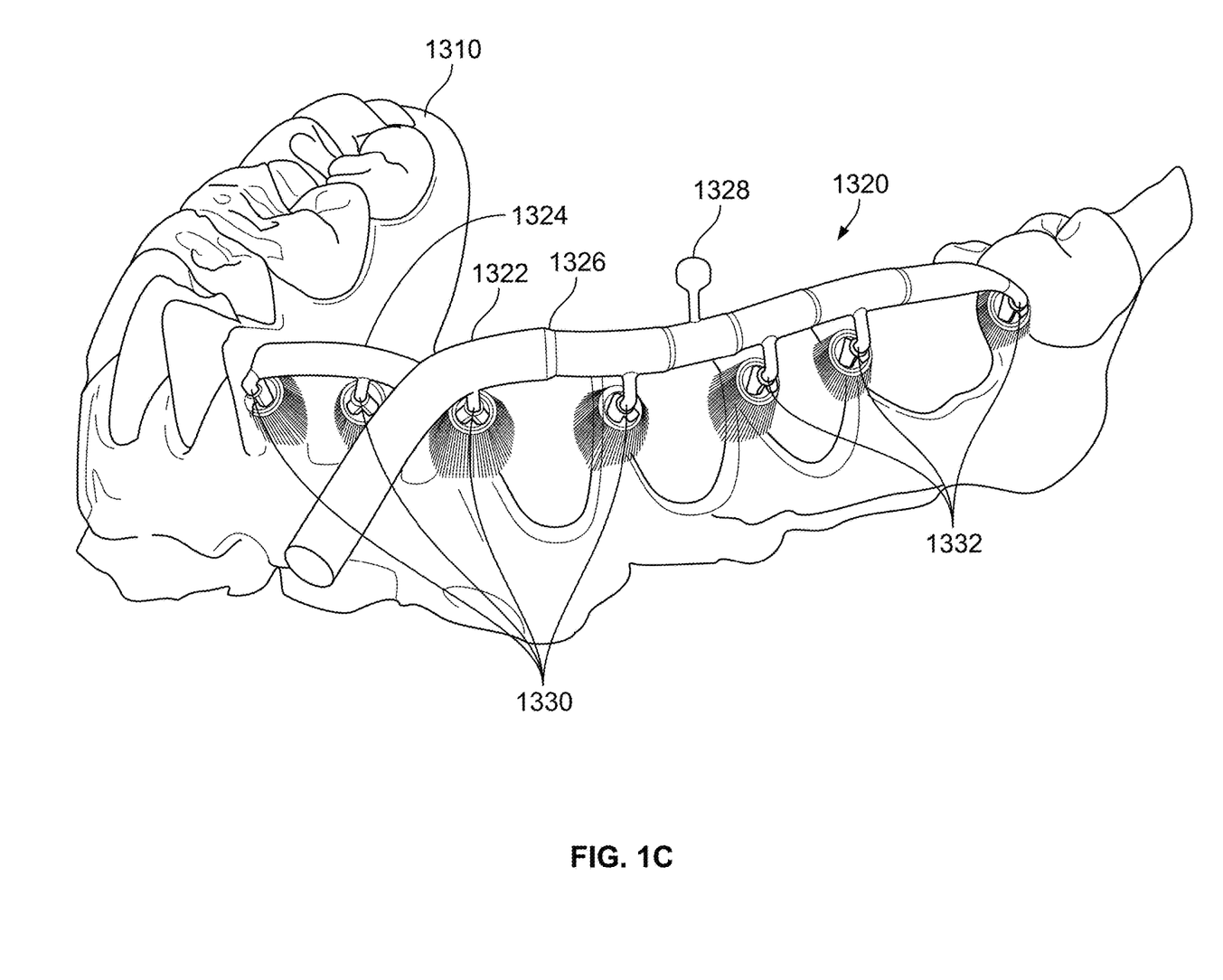
FIG. 1C depicts a schematic perspective view of a manifold relative to oral anatomy in accordance with some embodiments.

FIG. 1C depicts a schematic perspective view of a manifold relative to oral anatomy in accordance with some embodiments. The manifold 1320 may be coupled to a set of fluid nozzles 1330 comprising a set of fluid clearance geometries 1332. The manifold 1320 may comprise one or more of a trunk 1322, branch 1324, step region 1326, and flow balancing port 1328. The trunk 1322 may be a primary fluid conduit coupled between a fluid inlet port (not shown) and each of a branch 1324, flow balancing port 1328, and fluid nozzles 1330. The trunk 1322 may comprise a larger diameter than any of the branch 1324, flow port 1328, and fluid nozzles 1330. The branch 1324 may extend from the trunk 1322 and comprise a diameter smaller than the trunk 1322. The branch 1324 may serve as a secondary fluid conduit extending from a trunk 1322 for fluid nozzles 1330 not otherwise coupled to the trunk 1322. For example, a branch 1324 may extend from the trunk 1322 in FIG. 1C for fluid nozzles 1330 corresponding to a set of anterior teeth of a patient. Branches may be useful to reduce tortuosity (e.g., prevent kinks) in the manifold 1320 and improve hydraulic performance of the oral insert. In some variations, one or more flow balancing ports 1328 may extend from one or more of trunks 1322 and branches 1324. A flow balancing port 1328 may be configured to release pressure as fluid flows through the manifold 1320. Without flow balancing ports 1328, the manifold 1320 and fluid nozzles 1330 may generate uneven fluid flow. In some variations, a flow balancing port 1328 may be useful when a number of nozzles on all manifolds is not equal in order to maintain a predetermined range of hydraulic pressures. For example, a first manifold may include eight fluid nozzles and a second manifold may include seven fluid nozzles and one flow balancing port. The location and size of the pressure port may be designed such that a flow rate of fluid exiting the eight fluid nozzles associated with the first manifold is the same flow rate of fluid exiting the seven fluid nozzles associated with the second manifold.

In some variations, a diameter of the manifold 1320 may decrease along a length of the manifold 1320 due to a pressure gradient along a length of the manifold 1320. In some embodiments, the diameter of the manifold 1320 decreases in a continuous manner. The diameter of the manifold 1320 may decrease at a particular angle. In some embodiments, the diameter of the manifold 1320 decreases in a stepped manner. For example, the diameter of the manifold 1320 may have a first diameter between a first fluid nozzle and a second nozzle and a second diameter between the second nozzle and a third nozzle. In some variations, the number, shape, size, and location of the flow balancing port 1328 may be configured to promote a predetermined range of pressures through at least a portion of the manifold 1320. For example, one or more pressure ports 1328 may be configured such that a fluid pressure within the manifold 1320 may be within a predetermined range (e.g., relatively constant) throughout a length of the manifold 1320. In some variations, a flow balancing port 1328 may be located downstream of a step region 1326 of the manifold 1320. In some embodiments, the length of at least one manifold is different than the other manifolds. However, the flow rate of fluid exiting a fluid nozzle on each of the plurality of manifolds should be the same within a predetermined threshold tolerance. One or more pressure ports may be added to a manifold to increase a flow rate associated with the fluid nozzles associated with the manifold to match the flow rate of the fluid nozzles associated with the other manifold(s).

Figure 2:
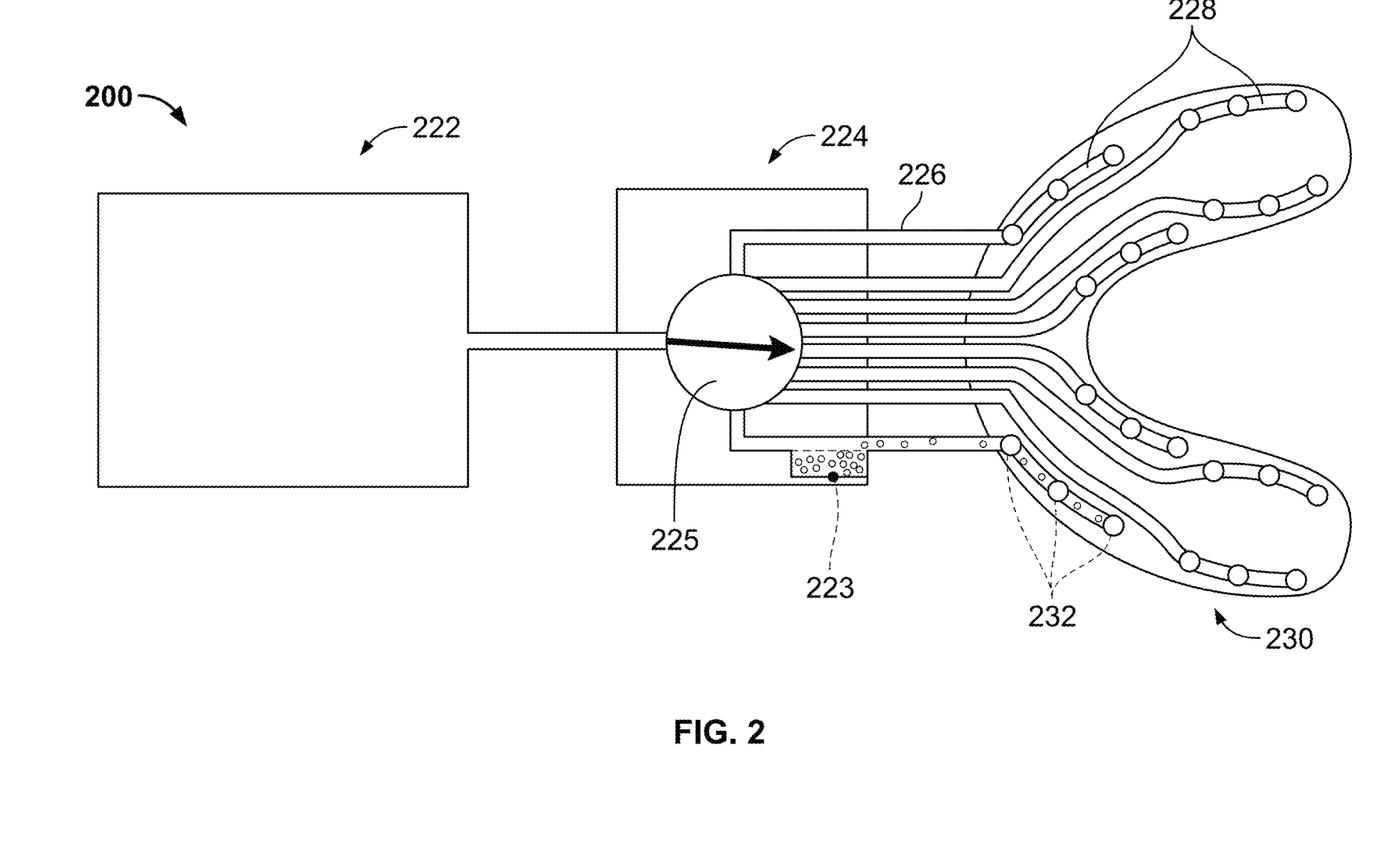
FIG. 2 is a diagram illustrating a system for cleaning the oral anatomy of a user in accordance with some embodiments.

FIG. 2 is a diagram illustrating a system for cleaning the oral anatomy of a user in accordance with some embodiments. In the example shown, system 200 includes a fluid reservoir 222, a pump 224 that has a switching manifold 225 that alternates connectivity between the fluid reservoir 222 and the separate fluid conduits 226 that are in communication with separate manifolds 228 of an oral insert 230. An additive may be introduced to an individual manifold 228 via a cartridge 223 inserted into the desired manifold in the mouthpiece or handle.

Figure 3A:
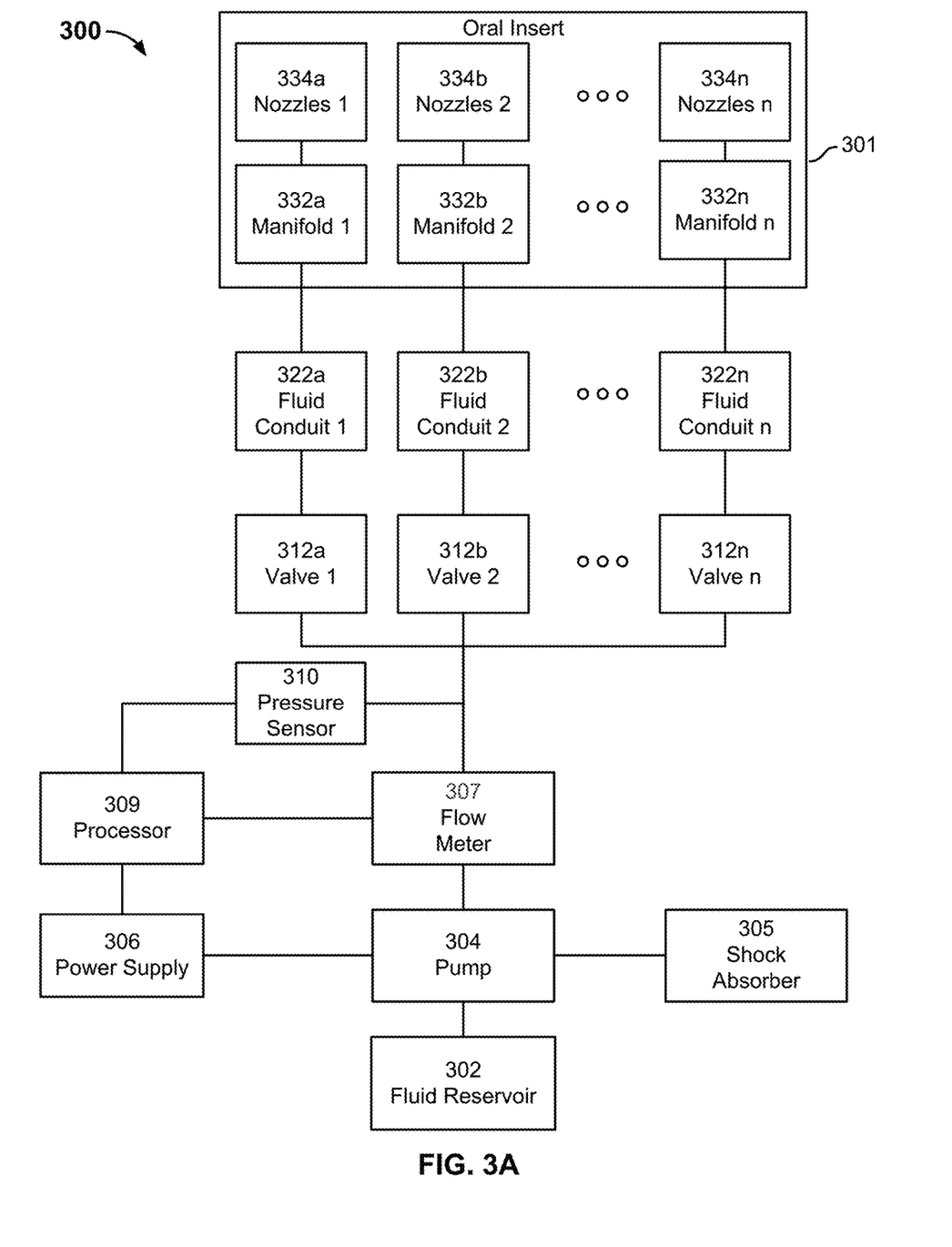
FIG. 3A depicts a block diagram of a system for testing the performance of an oral insert in accordance with some embodiments.

FIG. 3A depicts a block diagram of a system for testing the performance of an oral insert in accordance with some embodiments. In the example shown, system 300 includes a fluid reservoir 302 coupled to pump 304. Pump 304 is connected to power supply 306. Power supply 306 is configured to provide an input voltage to pump 304. Power supply 306 is connected to processor 309. Processor 309 is configured to control the input voltage that power supply 306 provides to pump 304. Pump 304 is connected to flow meter 307 and configured to provide fluid from fluid reservoir 302 to oral insert 301. Flow meter 307 is configured to measure a flow rate associated with providing the fluid from fluid reservoir 302 to oral insert 301. The flow rate depends on the input voltage provided from power supply 306 to pump 304. Pressure sensor 310 is configured to measure a pressure associated with providing fluid from fluid reservoir 302 to oral insert 301. The measured pressure depends on the input voltage (or current) provided from power supply 306 to pump 304. The outputs of flow meter 307 and pressure sensor 310 are provided to processor 309. Processor 309 is configured to generate a PQ curve (pressure-flow) based on the outputs of flow meter 307 and pressure sensor 310. Pump 304 may be coupled to shock absorber 305. Pump 304 may provide a pulsatile flow of fluid from fluid reservoir 302 to oral insert 301. Shock absorber 305 is utilized to smooth out the pulsations generated by pump 304.

Figure 3B:
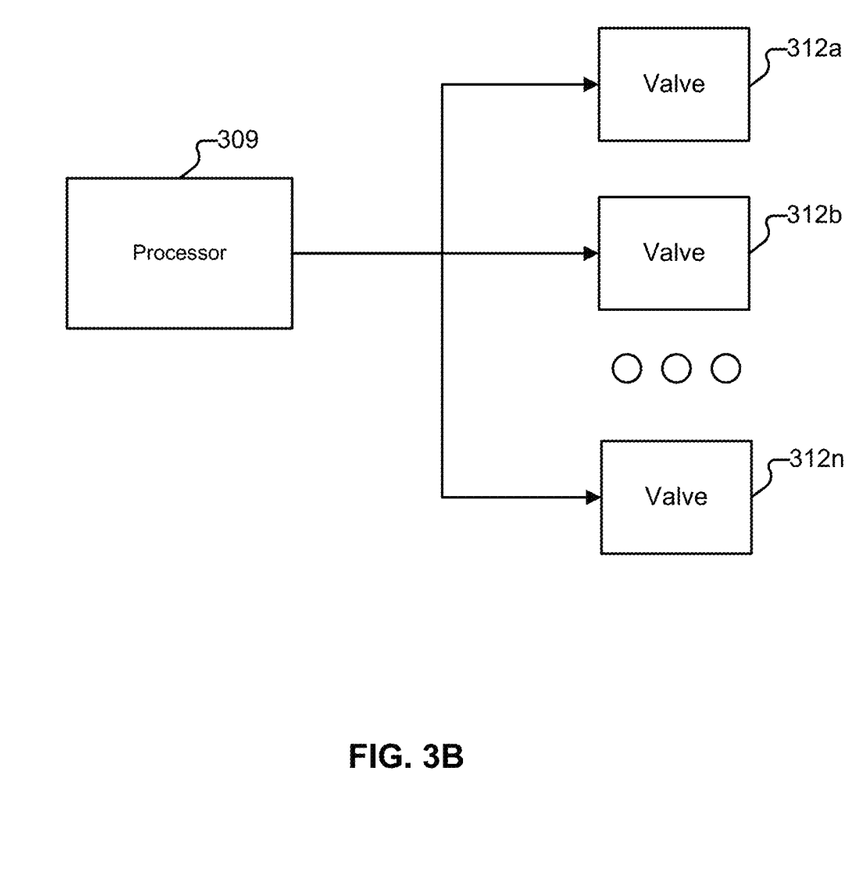
FIG. 3B depicts a block diagram of a subsystem for testing the performance of an oral insert in accordance with some embodiments.

As seen in FIG. 3B, processor 309 is connected to valves 312a, 312b, ..., 312n. Although FIGS. 3A and 3B depict processor 309 being connected to three valves, processor 309 may be connected to n valves. Each valve is associated with a corresponding manifold of oral insert 301.

The performance of oral insert 301 is verified by individually and sequentially testing each of the manifolds 332a, 332b, ..., 332n. Although FIG. 3A depicts oral insert 301 having three manifolds, oral insert 301 may have n manifolds. Each manifold of the manifolds 332a, 332b, ..., 332n is associated with a corresponding set of fluid nozzles 334a, 334b, ..., 334n. In one embodiment, oral insert 301 includes eight manifolds, each manifold having a set of eight fluid nozzles.

A number of fluid nozzles associated with a manifold may be different than a number of fluid nozzles associated with one or more other manifolds. For example, manifold 332a may be associated with a set of fluid nozzles 334a that includes seven fluid nozzles and manifold 332b may be associated with a set of fluid nozzles 334b that includes eight fluid nozzles. This may cause uneven fluid flow from the fluid nozzles, that is, the flow rate associated with manifold 332a is different than the flow rate associated with manifold 332b. This may cause discomfort, or inconsistent cleaning for the user using oral insert 301 during a cleaning process.

When at least one manifold includes a number of fluid nozzles that is different than the number of fluid nozzles associated with the other manifolds associated with oral insert 301, the manifold(s) having the different number of fluid nozzles may include one or more flow balancing ports to prevent uneven fluid flow from the fluid nozzles. A flow balancing port may be configured to release excess fluid as fluid flows through the manifold.

The manifolds 332a, 332b, ..., 332n may be tested by selecting one of them and generating a PQ curve for the selected manifold. Valves 312a, 312b, ..., 312n have a default state of closed. Processor 309 is configured to send a control signal to the valve associated with the selected manifold to change the state of the valve from a closed state to an open state. In some embodiments, valves 312a, 312b, ..., 312n are substituted for a switching manifold, such as switching manifold 225.

Fluid is provided to the selected manifold at a plurality of different pressures. The fluid pressure within the selected manifold is controlled by processor 309, which adjusts an input voltage (or input current) associated with pump 304. In some embodiments, manifold 332a is selected and fluid is provided from fluid reservoir 302 to the set of fluid nozzles 334a via valve 312a, fluid conduit 322a, and manifold 332a. In some embodiments, manifold 332b is selected and fluid is provided from fluid reservoir 302 to the set of fluid nozzles 334b via valve 312b, fluid conduit 322b, and manifold 332b. In some embodiments, manifold 332n is selected and fluid is provided from fluid reservoir 302 to the set of fluid nozzles 334n via valve 312n, fluid conduit 322n, and manifold 332n.

A PQ curve associated with the selected manifold is generated by determining a flow rate associated with the manifold and a pressure associated with the manifold at the plurality of input voltages associated with power supply 306. When fluid is provided from fluid reservoir 302 to a selected manifold, flow meter 307 and pressure sensor 310 are configured to provide a plurality of measurements to processor 309. At each input voltage (or input current), processor 309 is configured to wait for a steady state associated with the fluid being provided from fluid reservoir 302 (e.g., 1 second) to the selected manifold before determining the flow rate associated with the manifold and the pressure associated with the manifold.

Processor 309 is configured to generate the PQ curve associated with the selected manifold based on the determined flow rates and determined pressures. Processor 309 is configured to compare the PQ curve associated with the selected manifold to an upper limit curve and a lower limit curve. The selected manifold and its associated fluid nozzles are determined to be functional in the event the PQ curve is bounded within the upper limit curve and the lower limit curve. The selected manifold and its associated fluid nozzles are determined to be defective in the event at least one point of the PQ curve is outside of the upper limit curve and/or the lower limit curve.

Processor 309 may repeat the above process for each of the remaining manifolds of oral insert 301. However, if a tested manifold is determined to be defective and there are one or more other remaining manifolds to be tested, then oral insert 301 is determined to be defective. The one or more other remaining manifolds do not need to be tested. As a result, the amount of time and resources needed to verify the performance of oral insert 301 may be reduced. Oral insert 301 is determined to be operational in response to determining that the corresponding PQ curves associated with each of the manifolds 332a, 332b, ..., 332n are bounded by the upper limit curve and the lower limit curve.

Figure 4:
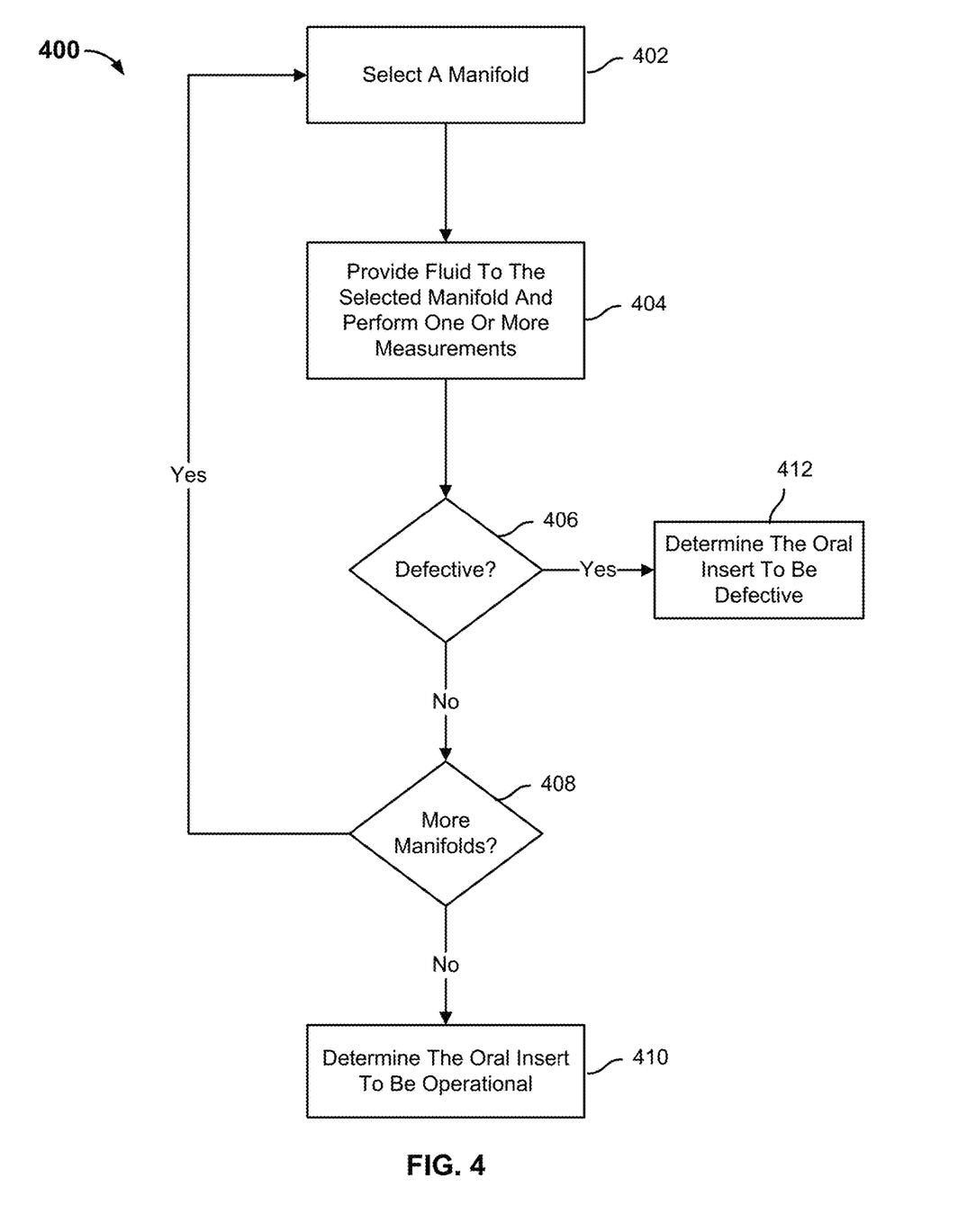
FIG. 4 is a flow diagram illustrating a process of testing the performance of an oral insert in accordance with some embodiments.

FIG. 4 is a flow diagram illustrating a process of testing the performance of an oral insert in accordance with some embodiments. In the example shown, process 400 may be implemented by a processor, such as processor 309.

At 402, a manifold of a plurality of manifolds associated with an oral insert is selected. The oral insert is comprised of a plurality of manifolds. Each manifold includes one or more fluid nozzles. The oral insert is configured to receive pressurized fluid at the fluid inlet port from a fluid reservoir via a pump. The oral insert is designed in a manner such that the fluid pressure within each of the manifolds is within a predetermined range throughout a length of a manifold. As a result, a flow rate associated with each of the fluid nozzles is designed to be the same within a threshold tolerance. That is, the performance of each of the manifolds and associated nozzles is expected to be the same within the threshold tolerance.

In some embodiments, a number of fluid nozzles associated with one of the manifolds is different than a number of fluid nozzles associated with the other manifolds. When at least one manifold includes a number of fluid nozzles that is different than the number of fluid nozzles associated with the other manifolds associated with the oral insert, the manifold(s) having the different number of fluid nozzles may include one or more flow balancing ports to prevent unbalanced pressure drops and uneven fluid flow from the fluid nozzles.

Each of the manifolds is associated with a corresponding valve. The manifold valves have a default state of closed. The processor sends a control signal to the valve associated with the selected manifold. In response, the valve associated with the selected manifold changes from a closed state to an open state while the valves associated with the non-selected manifolds remain in a closed state.

At 404, fluid is provided to the selected manifold and one or more measurements are performed. The flow rate associated with fluid exiting the fluid nozzles associated with the selected manifold may be adjusted based on an input voltage associated with a pump. The processor may send control signals to the pump to adjust the input voltage. In response, the pump causes the fluid provided from the fluid reservoir to the selected manifold to have a different inlet pressure.

A PQ curve for the manifold is generated based on the input voltages associated with the pump. At each input voltage, a flow rate associated with the selected manifold and a pressure associated with the selected manifold are determined. At each input voltage, the processor is configured to wait for a steady state associated with the fluid being provided from the fluid reservoir to the selected manifold before determining the flow rate associated with the selected manifold and the pressure associated with the selected manifold. The determined flow rates and pressures are utilized by the processor to generate the PQ curve for the selected manifold.

At 406, it is determined whether the selected manifold is defective based on the one or more measurements. The PQ curve associated with a manifold is expected to be within an upper bound curve and a lower bound curve. The selected manifold and its associated fluid nozzles are determined to be functional in the event the PQ curve is bounded within the upper limit curve and the lower limit curve. That is, the actual performance of the selected manifold matches an expected performance of a manifold within a threshold tolerance. The selected manifold and its associated fluid nozzles are determined to be defective in the event at least one point of the PQ curve is outside of the upper limit curve and/or the lower limit curve. Defects may include occluded manifold passages, occluded nozzles, or improperly produced nozzle geometry such as having the nozzle opening being oversized or undersized.

In response to a determination that the selected manifold is defective, process 400 proceeds to 412. In response to a determination that the selected manifold is not defective, process 400 proceeds to 408.

At 408, it is determined whether there are any more manifolds to analyze. In response to a determination that there is at least one more manifold to analyze, process 400 returns to step 402. In response to a determination that there are no more manifolds to analyze, process 400 proceeds to step 410.

At 410, the oral insert is determined to be operational. The oral insert is determined to be operational in response to determining that the corresponding PQ curves associated with each of the manifolds are bounded by the upper limit curve and the lower limit curve.

At 412, the oral insert is determined to be defective. In some embodiments, if a manifold is determined to be defective and there are one or more other remaining manifolds to be tested, the oral insert is determined to be defective. The one or more other remaining manifolds do not need to be tested. As a result, the amount of time and resources needed to verify the performance of the oral insert may be reduced.

Figure 5:
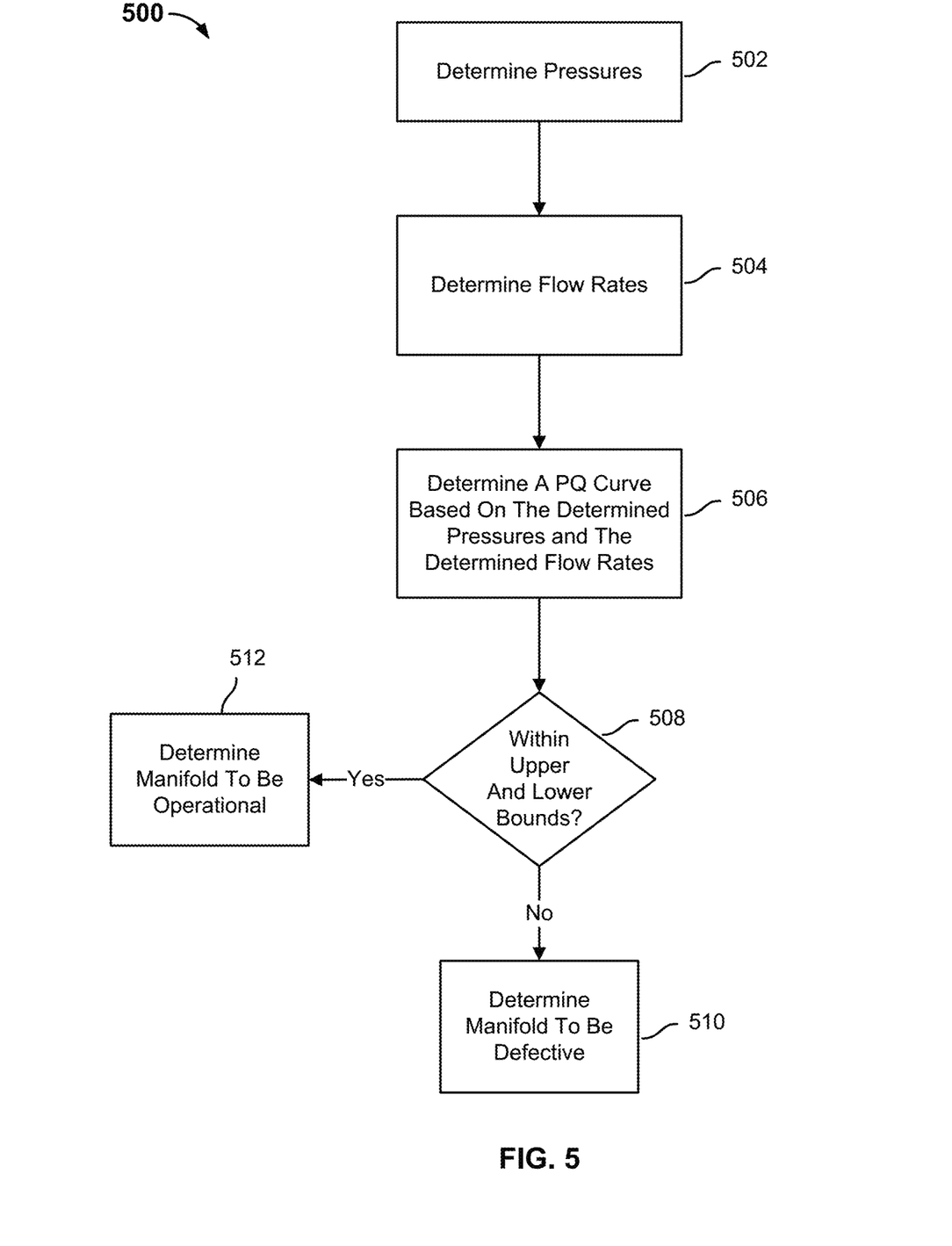
FIG. 5 is a flow diagram illustrating a process of testing the performance of a manifold in accordance with some embodiments.

FIG. 5 is a flow diagram illustrating a process of testing the performance of a manifold in accordance with some embodiments. In the example shown, process 500 may be implemented by a processor, such as processor 309. In some embodiments, process 500 is implemented to perform some or all of step 406 of process 400.

At 502, pressures associated with providing a fluid to a manifold are determined. A pump causes the fluid to be provided from a fluid reservoir to the manifold. The pressure associated with the fluid being provided from the fluid reservoir to the manifold is controlled by an input voltage associated with a pump. A conduit is located between an output of the pump and an input of the manifold. A pressure sensor may be coupled to the conduit. The pressure sensor provides one or more pressure measurements associated with the conduit to a processor. At each input voltage, the processor is configured to wait for a steady state associated with the fluid being provided from the fluid reservoir to the manifold before determining the pressure associated with the selected manifold.

At 504, flow rates associated with providing the fluid to the manifold are determined. A flow sensor is located between the pump and the manifold. The flow sensor is configured to measure a flow rate of the fluid being provided to the manifold. The flow sensor is configured to provide flow rate measurements to the processor. At each input voltage, the processor is configured to wait for a steady state associated with the fluid being provided from the fluid reservoir to the manifold before determining the flow rate associated with the manifold.

At 506, a PQ curve is determined based on the determined pressures and the determined flow rates. At each input voltage, a corresponding pressure and a corresponding flow rate is determined. Measurements are performed at a plurality of input voltages. The PQ curve is generated based on the measurements.

At 508, it is determined whether there is at least one point on the PQ curve that is not within the upper and lower bounds. In response to a determination that there is at least one point on the PQ curve that is not within the upper and lower bounds, process 500 proceeds to step 510. In response to a determination that there is not at least one point on the PQ curve that is not within the upper and lower bounds, process 500 proceeds to step 512.

Figure 6A:
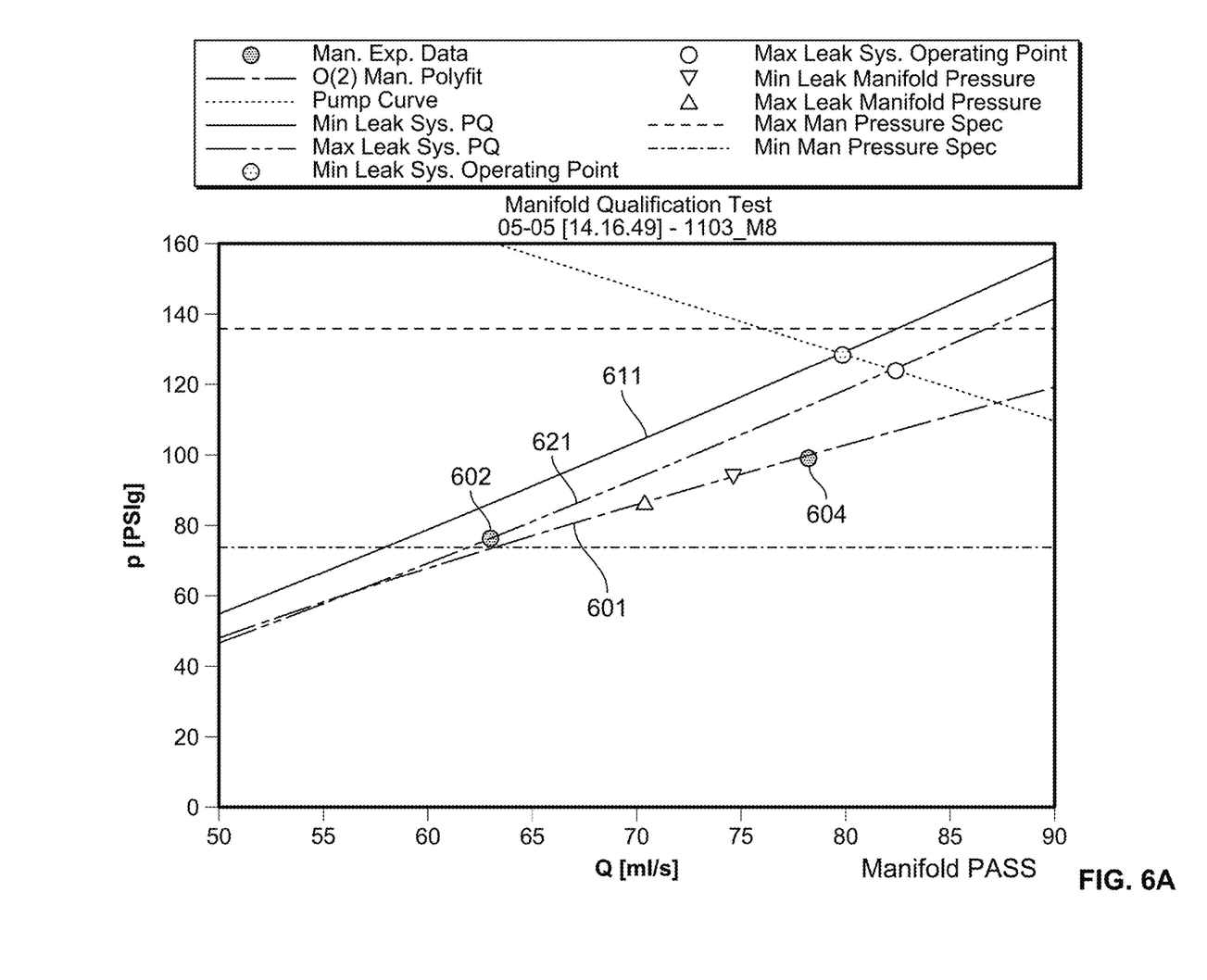
FIGS. 6A, 6B, 6C are examples of PQ curves.
Figure 6B:
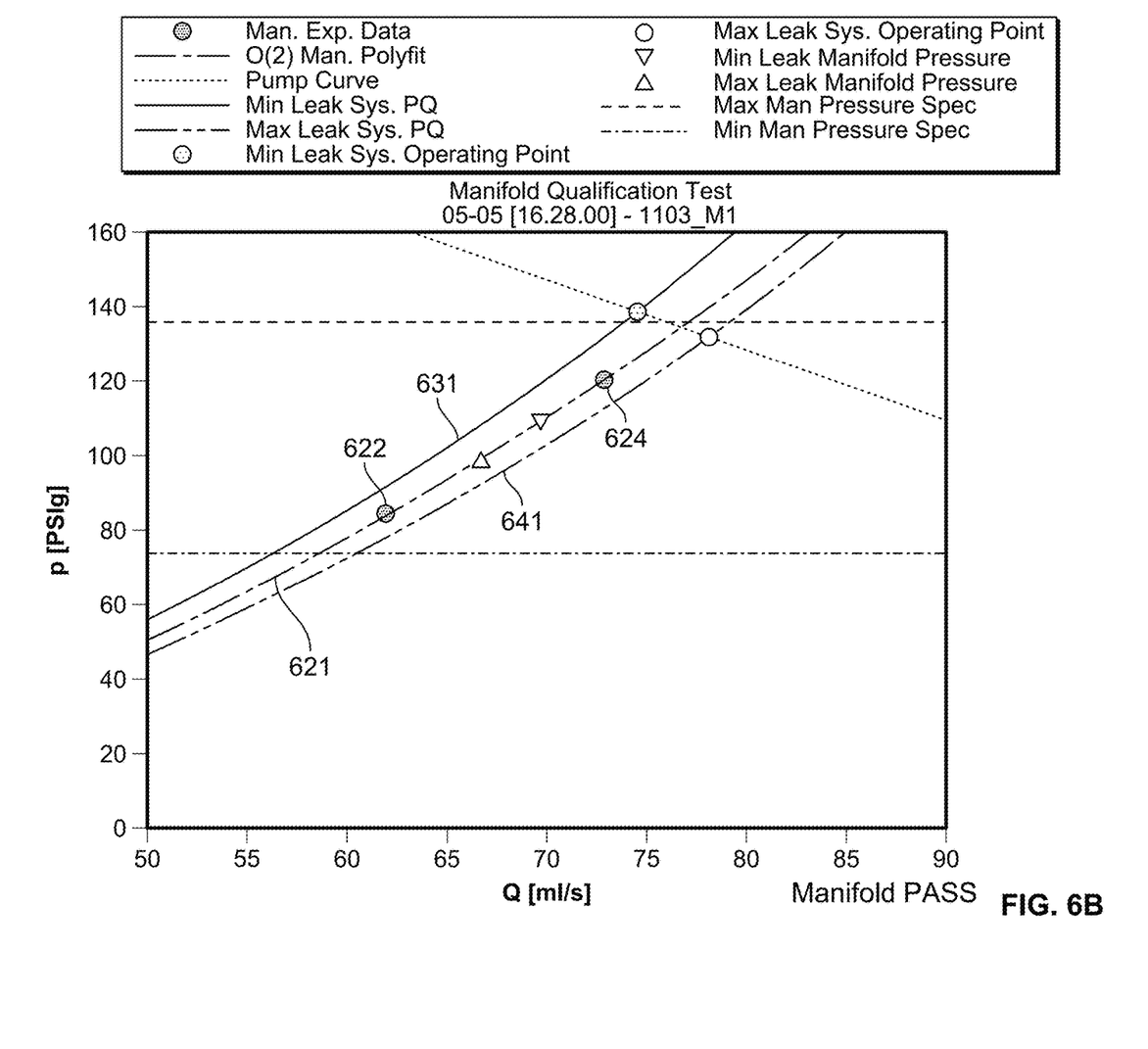
Figure 6C:
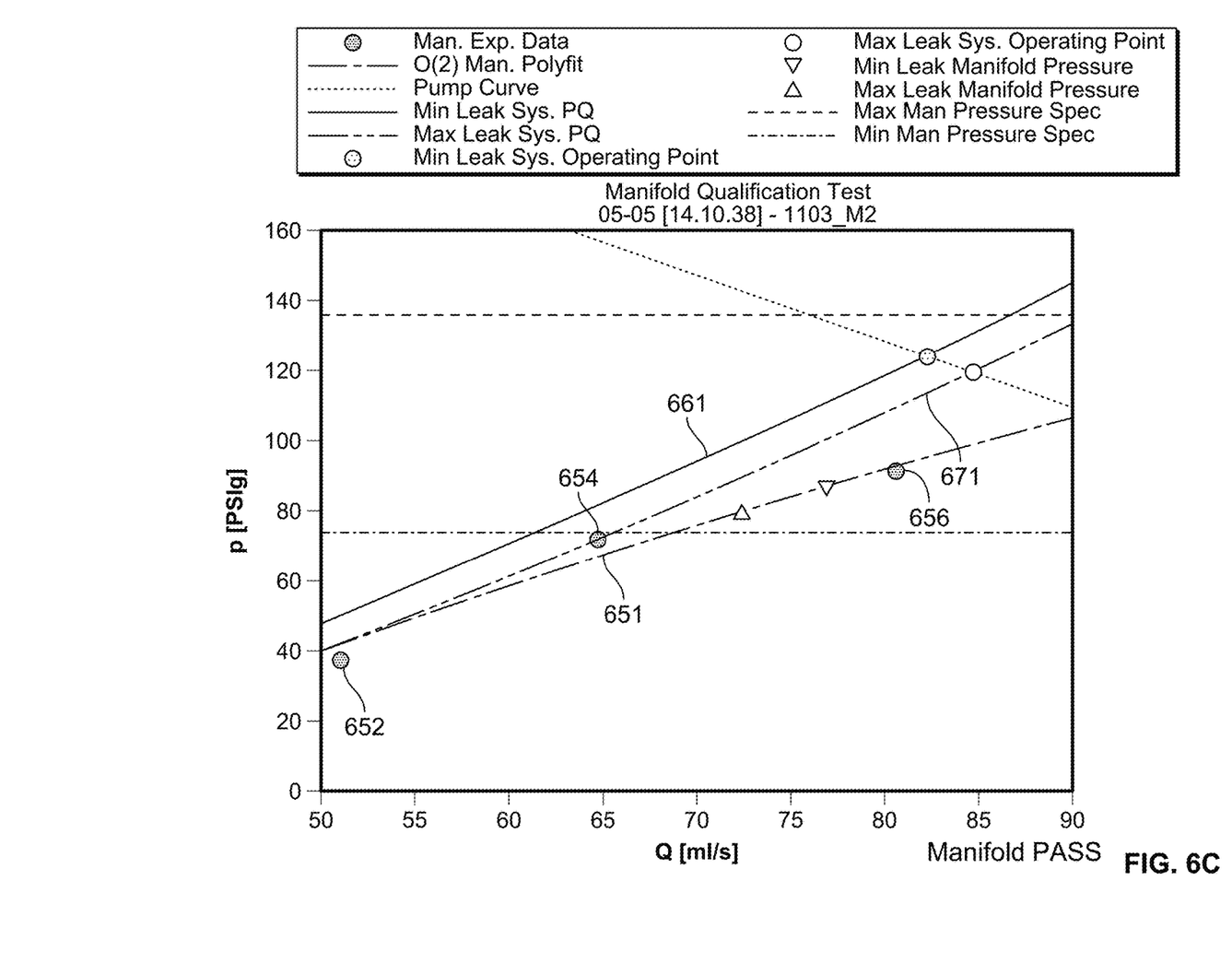

At 510, the manifold is determined to be defective.
At 512, the manifold is determined to be operational.
FIGS. 6A, 6B, 6C are examples of PQ curves. The PQ curves may be generated by a system for testing the performance of a manifold, such as system 300. In FIG. 6A, the PQ curve 601 was generated based on measurement points 602, 604. As seen in FIG. 6A, the PQ curve 601 is not bounded by the upper limit curve 611 and the lower limit curve 621. As a result, the manifold is determined to be defective.

In FIG. 6B, the PQ curve 621 was generated based on measurement points 622, 624. As seen in FIG. 6B, the PQ curve 621 is bounded by the upper limit curve 631 and the lower limit curve 641. As a result, the manifold is determined to be operational.

In FIG. 6C, the PQ curve 651 was generated based on measurement points 652, 654, 656. As seen in FIG. 6C, the PQ curve 651 is not bounded by the upper limit curve 661 and the lower limit curve 671. As a result, the manifold is determined to be defective.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method of verifying a performance of an oral insert, comprising:
    selecting a manifold of a plurality of manifolds associated with the oral insert, wherein each of the plurality of manifolds is associated with a same expected performance within a threshold tolerance;
    testing a performance of the manifold in part by:
        providing a liquid to the manifold selected among the plurality of manifolds associated with the oral insert, wherein the manifold includes a set of nozzles;
        determining an actual performance of the manifold by providing the liquid to the manifold at a plurality of different flow rates, performing corresponding measurements at the plurality of different flow rates including by determining a corresponding pressure at the plurality of different flow rates, and generating a pressure-flow curve for the manifold based on the corresponding measurements;
        comparing the generated pressure-flow curve for the manifold to an upper limit curve and a lower limit curve that represent boundaries of an operational oral insert;
        verifying a performance of each nozzle included in the set of nozzles associated with the oral insert based on whether the generated pressure-flow curve for the manifold is bounded by the upper limit curve and the lower limit curve; and
        determining that the manifold is defective in response to the generated pressure-flow curve for the manifold not being bounded by the upper limit curve and the lower limit curve; and
    in response to determining that the generated pressure-flow curve for the manifold not being bounded by the upper limit curve and the lower limit curve:
        forgoing testing of one or more remaining manifolds associated with the oral insert; and
        determining the oral insert to be defective.

2. The method of claim 1, wherein one or more other manifolds of the plurality of manifolds includes a corresponding set of nozzles.

3. The method of claim 2, wherein a number of nozzles included in the set of nozzles is different than a corresponding number of nozzles included in the corresponding set of nozzles.

4. The method of claim 3, wherein the manifold includes one or more flow balancing ports.

5. The method of claim 1, wherein a pump causes the liquid to be provided from a liquid reservoir to the manifold.

6. The method of claim 5, wherein the liquid is provided from the liquid reservoir to the manifold at a plurality of different input voltages associated with the pump.

7. The method of claim 6, wherein the corresponding pressure and a corresponding flow rate are determined at each of the plurality of different input voltages associated with the pump.

8. The method of claim 7, wherein the corresponding pressure and the corresponding flow rate determined at each of the plurality of different input voltages associated with the pump are utilized to generate the pressure-flow curve for the manifold.

9. The method of claim 8, wherein the manifold is determined to be operational in response to determining that the generated pressure-flow curve for the manifold is bounded by the upper limit curve and the lower limit curve.

10. The method of claim 8, wherein the manifold is determined to be defective in response to determining that at least one point associated with the generated pressure-flow curve for the manifold is not bounded by the upper limit curve and the lower limit curve.

11. The method of claim 1, further comprising verifying a performance of a previously selected manifold in response to determining that the actual performance of the previously selected manifold of the plurality of manifolds matches the same expected performance within the threshold tolerance.

12. The method of claim 1, wherein the actual performance of the manifold is determined when the liquid provided to the manifold is at a steady state.

13. A system, comprising:
    a processor configured to:
        select a manifold of a plurality of manifolds associated with an oral insert, wherein each of the plurality of manifolds is associated with a same expected performance within a threshold tolerance;
        test a performance of the manifold in part by:
            causing a liquid to be provided to the manifold selected among the plurality of manifolds associated with the oral insert, wherein the manifold includes a set of nozzles;
            determining an actual performance of the manifold by providing the liquid to the manifold at a plurality of different flow rates, performing corresponding measurements at the plurality of different flow rates including by determining a corresponding pressure at the plurality of different flow rates, and generating a pressure-flow curve for the manifold based on the corresponding measurements;
            comparing the generated pressure-flow curve for the manifold to an upper limit curve and a lower limit curve that represent boundaries of an operational oral insert;
            verifying a performance of each nozzle included in the set of nozzles associated with the oral insert based on whether the generated pressure-flow curve for the manifold is bounded by the upper limit curve and the lower limit curve; and
            determining that the manifold is defective in response to the generated pressure-flow curve for the manifold not being bounded by the upper limit curve and the lower limit curve; and
        in response to determining that the generated pressure-flow curve for the manifold not being bounded by the upper limit curve and the lower limit curve:
            forgo testing of one or more remaining manifolds associated with the oral insert; and
            determine the oral insert to be defective; and
    a memory coupled to the processor and configured to provide the processor with instructions.

14. The system of claim 13, wherein one or more other manifolds of the plurality of manifolds includes a corresponding set of nozzles.

15. The system of claim 14, wherein a number of nozzles included in the set of nozzles is different than a corresponding number of nozzles included in the corresponding set of nozzles.

16. The system of claim 15, wherein the manifold includes one or more flow balancing ports.

17. The system of claim 13, further comprising:
a pump; and
a liquid reservoir, wherein the pump is configured to cause the liquid to be provided from the liquid reservoir to the manifold, wherein the processor is coupled to the pump and configured to control an input voltage at which the pump operates when the pump is providing the liquid from the liquid reservoir to the manifold.

18. The system of claim 17, wherein the liquid is provided from the liquid reservoir to the manifold at a plurality of different input voltages associated with the pump.

19. The system of claim 18, wherein the corresponding pressure and a corresponding flow rate are determined at each of the plurality of different input voltages associated with the pump.

20. The system of claim 19, wherein the corresponding pressure and the corresponding flow rate determined at each of the plurality of different input voltages associated with the pump are utilized to generate the pressure-flow curve for the manifold.

21. A computer program product embodied in a non-transitory computer readable medium and comprising computer instructions for:
selecting a manifold of a plurality of manifolds associated with an oral insert, wherein each of the plurality of manifolds is associated with a same expected performance within a threshold tolerance;
testing a performance of the manifold in part by:
providing a liquid to the manifold selected among the plurality of manifolds associated with the oral insert, wherein the manifold includes a set of nozzles;
determining an actual performance of the manifold by providing the liquid to the manifold at a plurality of different flow rates, performing corresponding measurements at the plurality of different flow rates including by determining a corresponding pressure at the plurality of different flow rates, and generating a pressure-flow curve for the manifold based on the corresponding measurements;
comparing the generated pressure-flow curve for the manifold to an upper limit curve and a lower limit curve that represent boundaries of an operational oral insert;
verifying a performance of the oral insert based on whether the actual performance of the manifold matches the same expected performance within the threshold tolerance; and
determining that the manifold is defective in response to the generated pressure-flow curve for the manifold not being bounded by the upper limit curve and the lower limit curve; and
in response to determining that the generated pressure-flow curve for the manifold not being bounded by the upper limit curve and the lower limit curve:
forgoing testing of one or more remaining manifolds associated with the oral insert; and
determining the oral insert to be defective.

* * * * *